United States Patent [19]

Cardenas et al.

[11] Patent Number: 4,484,007
[45] Date of Patent: Nov. 20, 1984

[54] PROCESS FOR PREPARATION OF ARYLTERPENOID INSECT MATURATION INHIBITORS

[75] Inventors: Carlos G. Cardenas; Tse-Lok Ho, both of Jacksonville; Shing-Hou Liu, Atlantic Beach, all of Fla.

[73] Assignee: SCM Corporation, New York, N.Y.

[21] Appl. No.: 488,281

[22] Filed: Apr. 25, 1983

Related U.S. Application Data

[63] Continuation-in-part of Ser. No. 448,230, Dec. 9, 1982, abandoned.

[51] Int. Cl.$^3$ .................. C07C 41/01; C07C 43/02
[52] U.S. Cl. .................................. 568/628; 568/626; 568/715
[58] Field of Search .................. 568/715, 626, 628; 424/339

[56] References Cited

U.S. PATENT DOCUMENTS

| | | | |
|---|---|---|---|
| 2,902,495 | 9/1959 | Webb | 260/348 |
| 3,700,746 | 10/1972 | Takacs | 260/675.5 |
| 3,700,747 | 10/1972 | Takacs | 260/675.5 |
| 3,780,124 | 12/1973 | Davis | 260/675.5 |
| 3,780,125 | 12/1973 | Takacs | 260/675.5 |
| 3,825,661 | 7/1974 | Emmick | 424/278 |
| 3,873,724 | 3/1975 | Beroza et al. | 424/341 |
| 3,904,773 | 9/1975 | Schwartz et al. | 424/304 |
| 3,914,260 | 10/1975 | Schwartz et al. | 260/348 A |
| 3,933,865 | 1/1976 | Schwartz et al. | 260/348 A |
| 3,978,230 | 8/1976 | Schwartz | 424/331 |
| 3,982,014 | 9/1976 | Schwartz et al. | 424/300 |
| 4,002,769 | 1/1977 | Schwartz | 424/339 |

FOREIGN PATENT DOCUMENTS 154658 10/1904 Fed. Rep. of Germany ...... 568/626

OTHER PUBLICATIONS

Finkbeiner et al., "Synthetic Applications of the Titanium-Catalyzed Exchange of Olefins with Grignard Reagents", Jour. Org. Chem., 27, 3395-3400, 1962.
Farady et al., "Transition Metal Alkyls and Hydrides-Structure of Products Formed in the Reactions Between Olefins and Grignard Reagents in the Presence of Nickel Chloride", Journal Organometallic Chem., 28, (1971), 159-165.
Akutagawa et al., "Metal-Assisted Terpenoid Synthesis I. Regio-selective Isoprene Insertion into an Allyl-Magnesium Bond and the Application to Synthesis of Natural Terpenoids"; JACS, 97:23/Nov. 12, 1975.
Jpn. Kokai Tokkyo KoHO, JP 82 11,989, 01/21/82, Sato et al., CA 97:23995v, (Tetrahedron Letters, vol. 21, pp. 365-368).
Sato et al., "Cp$_2$TiCl$_2$-Catalyzed Grignard Exchange Reactions with Acetylenes-a convenient method for Preparation of E-alkenyl Grignard Reagents", Tetrahedron Letrs., vol. 22, pp. 85-88, 1981.
"Studies in the Terpene Series, XX, The Thermal Isomerization Pinane at Atmospheric Pressure", Pine et al.; JACS, vol. 76, pp. 4412-4415, 1954.

Primary Examiner—Werren B. Lone
Attorney, Agent, or Firm—R. A. Sturges; M. H. Douthitt

[57] ABSTRACT

There is provided an improved process for producing biologically active arylterpenoid compounds useful to inhibit eclosion of pupae, e.g., fly pupae or mosquito pupae. The process is characterized by reacting a terpenoid material having a terminal unsaturated linkage, e.g., dihydromyrcene (3,7-dimethylocta-1,6-diene) with a lower alkyl Grignard reagent, e.g., n-propyl magnesium chloride to form a Grignard exchange product. The exchange product is then benzylated. Either a benzyl halide, e.g., p-isopropylbenzyl chloride, or a benzaldehyde, e.g., p-isopropylbenzaldehyde may be used. These compounds are specifically described in U.S. Pat. No. 4,002,769. They contain also a lower alkoxy group, e.g., methoxy. This can be introduced prior to the formation of the Grignard exchange product or at a later stage in the operation. Use of the exchange-type Grignard reaction enables elimination of several steps when producing the arylterpenoids from pinene as the terpene source, and consequent costs.

49 Claims, No Drawings

PROCESS FOR PREPARATION OF ARYLTERPENOID INSECT MATURATION INHIBITORS

RELATED APPLICATION

This application is a continuation-in-part of our copending application Ser. No. 448,230 filed Dec. 9, 1982 now abandoned.

The present invention relates to improved processes for the production of certain arylterpenoid compounds useful as eclosion inhibiting agents, particularly for certain species of flies and certain species of mosquito. More specifically, the invention provides improved processes for making compounds described in U.S. Pat. No. 4,002,769 dated Jan. 11, 1977. The disclosure of U.S. Pat. No. 4,002,769 is incorporated herein by reference. The aforesaid disclosure provides the properties, the chemistry and the manner of using compounds produced by the improved process of the present invention. These compounds have also been found effective in the control of fire ants (C&EN Aug. 16, 1982, p. 27–29).

BACKGROUND OF THE INVENTION AND PRIOR ART

The arylterpenoid compounds produced by the processes hereof have a 2,6-dimethylnonane backbone and are substituted at the 2-position by a lower alkoxy group, e.g., methoxy, ethoxy, propoxy, isopropoxy, butoxy, isobutoxy, etc. At the 9-position of the nonane chain is an aryl substituent from which the compound in part derives its name. The aryl group, usually phenylene, preferably contains at least one substituent group directly connected to a ring carbon atom. For best results the substituent group is located in the position para to the point of attachment to the nonane chain. Consequently, the compounds produced in accordance herewith may be represented by the structural formula shown in the aforesaid patent:

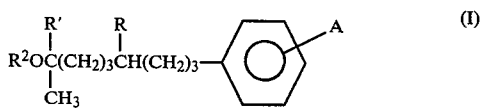
(I)

wherein A is a $C_1$–$C_5$ alkyl group, preferably ethyl, isopropyl, sec.-butyl, tertiary butyl; a $C_1$–$C_4$ alkoxy group, e.g., methoxy, ethoxy, isopropoxy; a $C_1$–$C_4$ thioalkoxy group, e.g., thioethoxy, nitro, or 3,4-methylene dioxy; more preferably A is in the para position, and most desirably A is in the para position and selected from $C_1$–$C_5$ alkyl; R and R' are independently methyl or ethyl, preferably methyl;, $R^2$ is a $C_1$–$C_4$ alkyl group, preferably methyl or ethyl, more desirably methyl. These compounds will inhibit eclosion of flies and mosquitos by several modes of application including application directly to the larvae or pupae, application to the natural growth media such as animal feces, incorporation in the diets of livestock and poultry and by spray application in appropriate animal housing areas.

A method of preparing the above compounds is disclosed in U.S. Pat. No. 4,002,769 proceeding through an ylid (phosphorane) plus citronellal to form a diene hydrocarbon. This is partially hydrogenated to a monoene and later alkoxylated to yield the final product. More recently, the methoxy derivative of citronellal has become commerically available. The alkoxylation when performed early avoids the final alkoxylation step as described in the above patent.

Methoxy citronellal can be prepared from geraniol according to the following scheme:

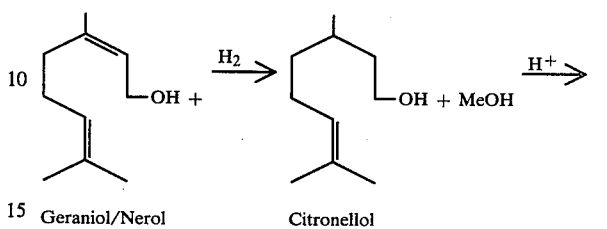

Geraniol/Nerol     Citronellol

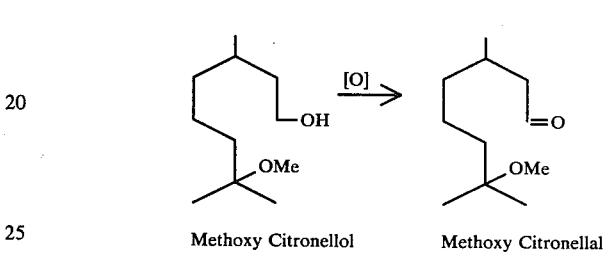

Methoxy Citronellol     Methoxy Citronellal

Geraniol/nerol can be produced from linalool according to the isomerization procedure described by Kane in U.S. Pat. No. 4,254,291. Linalool can be made from alpha-pinene by the following scheme:

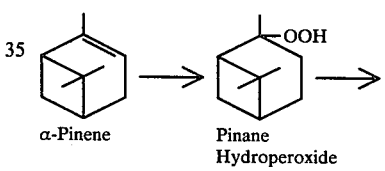

α-Pinene     Pinane Hydroperoxide

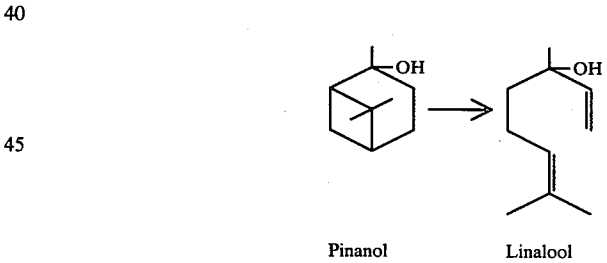

Pinanol     Linalool

A process for making arylterpenoid compounds may proceed by reacting methoxy citronellal with p-isopropylbenzyl magnesium chloride or bromide followed by dehydration and hydrogenation according to the following scheme:

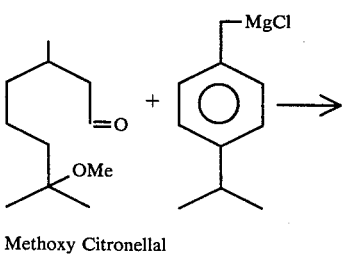

Methoxy Citronellal

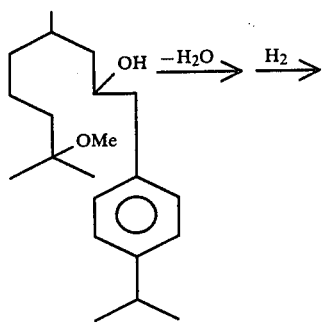

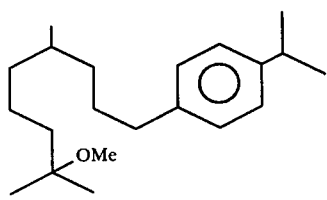

(I)

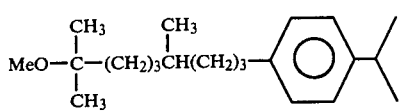

(I)

Alternatively, instead of using methoxycitronellal, methoxycitronellyl chloride or bromide can be made and converted to the magnesium chloride or bromide (Grignard) and the latter reacted with p-isopropylbenzaldehyde, dehydrated, and hydrogenated or hydrogenolyzed to yield (I) above.

We have found a much shorter and less expensive route to the formation of arylterpenoid compounds of the type described in the aforesaid U.S. Pat. No. 4,002,769. The success of the procedure depends on the application of a surprisingly effective obscure, albeit known (See Tetrahedron Letters, Vol. 22, pgs. 85–88 (1981)), Grignard exchange reaction whereby a lower alkyl Grignard reagent is exchanged with 3,7-dimethyl-1,6-octadiene (dihydromyrcene) or its derivatives. This is distinct from the normal Grignard formation reaction from halides. The presence of a remote alkoxy group in the dihydromyrcene structure not only does not inhibit the reaction, but appears to have a positive effect on the conversion. We are able moreover, to start with relatively inexpensive alpha or beta-pinene or a mixture thereof, and in a very few steps produce (I) above, instead of using the more numerous and costly steps involved in U.S. Pat. No. 4,002,769 or alternative procedures such as mentioned above.

BRIEF STATEMENT OF THE INVENTION

Briefly stated, therefore, the present invention is in a process for making biologically active arylterpenoids, and more specifically 2,6-dimethyl-2-alkoxy-9-aryl nonanes. The processes are characterized by the steps of reacting a 3,7-dimethyl-1,6-octadiene or a 7-alkoxy-3,7-dimethyloctene-1 with a lower alkyl Grignard reagent in the presence of a vanadium, zirconium, titanium, nickel, iron, or cobalt catalyst, e.g., $VCl_4$, $V(OR)_3$ (wherein R is $C_1$-$C_4$ alkyl), $ZrCl_4$, $TiCl_4$, $Cp_2TiCl_2$, $NiCl_2$, $FeCl_2$, $CoCl_2$, etc., (See Finkbeiner et al, J. Org. Chem. 27, 3395–3400, 1962) to form a Grignard exchange product while releasing a lower alkylene hydrocarbon; benzylating the resulting exchange product, and recovering the corresponding 2,6-dimethyl-9-aryl nonyl compound. If the molecule has not been previously alkoxylated, a lower alkoxy group may be introduced at this point in the preparation of the arylterpenoid. The products are normally liquid and soluble in hydrocarbon solvents, e.g., xylene, and can be dispersed in water together with such solvents, especially in the presence of a nonionic surface active agent, e.g., phenoxy polyethoxy ethanol (Triton X-100), for use in controlling eclosion of insects. In a specific embodiment, 25 parts of the active ingredient (for example, 2,6-dimethyl-2-methoxy-9-)p-isopropylphenyl)nonane) are dissolved in 65 parts of xylene and 10 parts of Triton X-100 to form a concentrate. This is dispersed in water in an amount sufficient to provide from 0.1 to 10 ppm of the active ingredient. This dispersion is then applied to the insect larvae by spray application.

DETAILED DESCRIPTION OF THE INVENTION AND SPECIFIC EXAMPLES

Dihydromyrcene (citronellene), also known as 3,7-dimethylocta-1,6-diene, a terpene hydrocarbon, or its 7-alkoxy derivatives, is conveniently used to form a Grignard by an exchange reaction in the presence of a vanadium, zirconium, titanium or Group VIII metal catalyst. The term "Grignard exchange catalyst" as used herein will be understood as including vanadium tetrachloride, trimethoxy vanadium, triethoxy vanadium, tri-isobutyl vanadate, zirconium tetrachloride, titanium tetrachloride and bis-(cyclopentadienyl) titanium dichloride, nickel dichloride and halides of the other Group VIII metals. Dihydromyrcene is readily derived from alpha or beta-pinene by hydrogenation in liquid or vapor phase to pinane using molecular $H_2$ and any suitable solid contact hydrogenation catalyst in a known manner (See Example II, U.S. Pat. No. 2,902,495 and Pines et al. "The Thermal Isomerization of Pinane at Atmospheric Pressure" JACS 76, 4412, 4415 (Exp. (1954) and pyrolysis in the vapor phase at an elevated temperature above 200° C., for example, 600°–620° C. to open the ring to yield dihydromyrcene according to the following scheme:

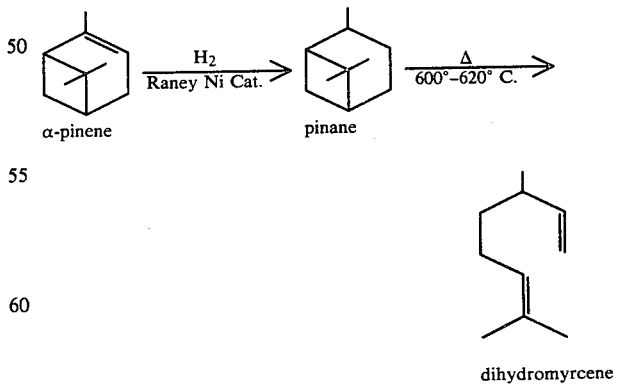

dihydromyrcene

We prefer to effect hydrogenation with molecular hydrogen under superatmospheric pressure, e.g., 70 to 80 psig. in the liquid phase and in the presence of a solid contact catalyst, e.g., Raney nickel until 1 mole of hydrogen per mole of pinene has been absorbed. However, any suitable hydrogenation procedure and catalyst may be used. Hydrogenation temperatures range from room temperature to upwards of 250° C. The pressure may range from atmospheric to as high as 350 atmospheres. At this point, the dihydromyrcene can be alkoxylated at the 6-7 double bond by any suitable known alkoxylation or thioalkoxylation procedure for example, by an acid catalyzed (e.g., HCl) reaction with a molar excess of a lower alkanol (e.g., methanol, ethanol, isopropanol, etc.) under reflux conditions. Stirring for a prolonged period at a temperature below atmospheric reflux temperature, e.g., 50° C., may also be used satisfactorily. Thus, methoxy or other $C_2$-$C_4$ alkoxy derivatives of dihydromyrcene may be prepared with the $OR^2$ group entering the molecule at the 7 position, where $R^2$ is lower alkyl, i.e., $C_1$-$C_4$. The temperature of alkoxylation is generally below about 110° C. Instead of lower alkanol, lower thioalkanol may be used. The term "lower" as applied to alkanols and alkyl herein means 1 to 4 carbons.

The dihydromyrcene, or 7-alkoxy dihydromyrcene, is then reacted at a temperature generally below about 120° C. at normal pressure with a lower alkyl magnesium halide, having the structure $R^4MgX$ where $R^4$ is lower alkyl and X is halogen, e.g., n-propyl magnesium chloride or bromide, isopropyl magnesium chloride or bromide, ethyl magnesium chloride or bromide, in the presence of a catalytic amount of Grignard exchange catalyst (from 0.01 mole to about 0.3 mole/mole of alkene-1—larger amounts of Grignard exchange catalyst can be used but are uneconomical), until evolution of alkene diminishes or ceases, i.e., when the equivalent of about one mole of alkene per mole of the dihydromyrcene or alkoxydihydromyrcene has been evolved. The preferred Grignard exchange catalysts are biscyclopentadienyltitaniumdichloride or vanadium tetrachloride. In this reaction it does not much matter which of the reactants is in molar excess. With an excess of the dihydromyrcene or alkoxydihydromyrycene, there is a necessary recovery of starting material. With an excess of the Grignard reagent, there is a tendency for the excess Grignard to react in the subsequent step. Hence, there is a cost trade-off, and consideration must be given to yield and to convenience. For our purposes, we prefer a slight molar excess of the Grignard, e.g., 1.05 moles of the Grignard to each mole of the dihydromyrcene or alkoxy dihydromyrcene, as follows:

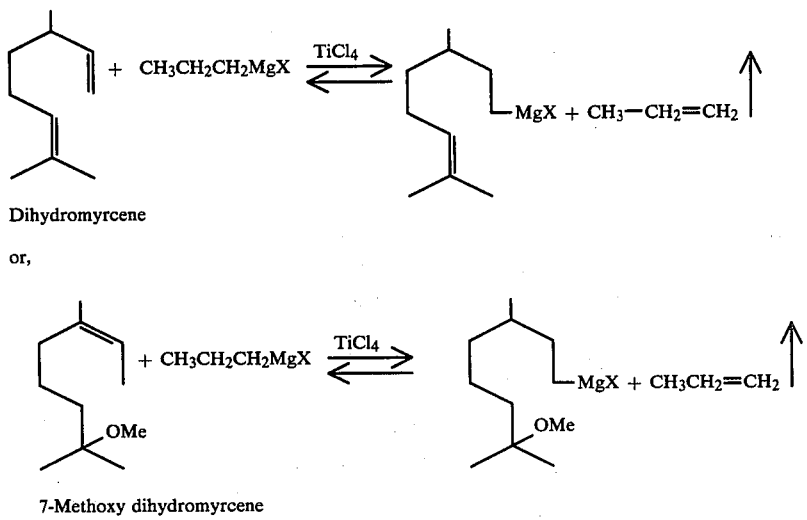

Dihydromyrcene or,

7-Methoxy dihydromyrcene

As indicated, the reaction goes substantially to completion to yield Grignard exchange product because the normal equilibrium is displaced by volatilization of the propylene from the reaction mass. In the foregoing reactions, X is a halogen, e.g., chlorine, bromine, iodine, etc.; chlorine or bromine are preferred. The reaction is conveniently carried out in a suitable solvent, for example, diethyl ether and/or tetrahydrofuran (THF) for a period of time sufficient to evolve propylene to an extent indicating substantial completion of the reaction, usually about 2-5 hours, e.g., 3 hours, at about 25° C. under an inert atmosphere, e.g., nitrogen, argon, or helium. The product is identified herein for convenience as a "Grignard exchange product".

The Grignard exchange product is now ready for alkylation with an aryl aldehyde or arylmethyl halide by any suitable known alkylation procedure to yield a precursor to the final product, or to yield the final product directly, i.e., the arylterpenoid compound. These reactions are conveniently and preferably carried out at low temperatures in the range of from about −20° C. to about 50° C., such as ether reflux temperature, or below room temperature, e.g., on an ice bath. Where the Grignard exchange product is reacted with an aryl aldehyde, e.g., p-cumyl aldehyde or p-isopropyl benzaldehyde, there is formed a benzylic alcohol derivative of the final product (II) in accordance with the following scheme:

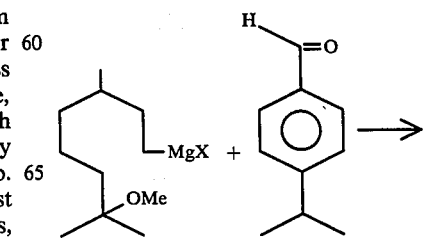

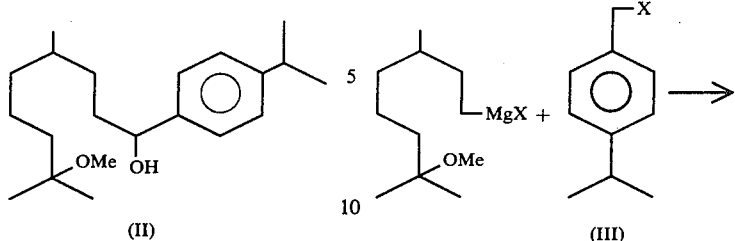

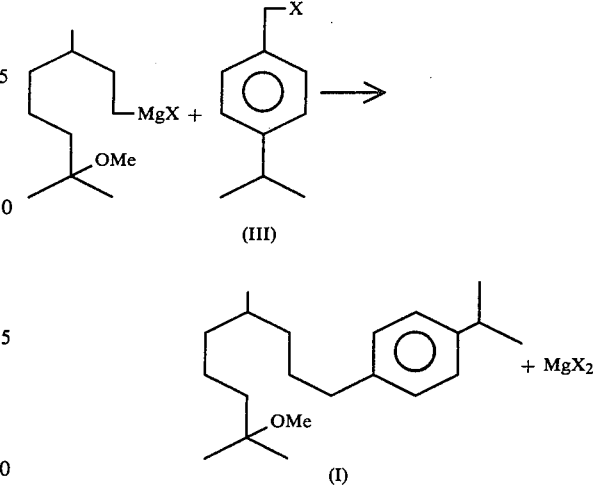

Hydrogenolysis of the benzylic alcohol group yields the desired arylterpenoid compound (I). Hydrogenolysis is a technique well known to those skilled in the art. In general, it involves treatment under hydrogenation conditions of the product, e.g., (II) above, with a catalytic amount, i.e., 2% to about 0.05% by weight of acid, e.g., HCl, $H_2SO_4$, p-toluene sulfonic acid, Amberlyst 15, or equivalent acid, for the purpose of weakening the C—O bond by protonation making it more susceptible to hydrolysis to remove water, and in the presence of molecular hydrogen and a catalytic amount of solid contact hydrogenation catalyst to saturate the double bond resulting when water is removed. The reaction is complete when 1 mole of $H_2$ per mole of product, e.g., (II) above has been absorbed. Hydrogenolysis is accomplished in a single step and is carried out broadly in a temperature range of from 0° C. to 200° C., preferably room temperature to 100° C. and at a pressure in the range of atmospheric to 75 atmospheres, and most usually in the range of 1 to 20 atmospheres. The solid hydrogenation catalysts are those well known in the art of hydrogenation examples of which are mentioned above. The hydrogenation is continued until hydrogen is no longer sufficiently rapidly absorbed as indicated, for example, by stability of hydrogen pressure.

Alternatively, the reactions of hydrogenolysis, namely, dehydration and hydrogenation may be carried out sequentially. Thus, dehydration of (II) above followed by hydrogenation yields (I). A catalytic amount of a dehydrating agent, e.g., p-toluene sulfonic acid, sulfuric acid, sulfonated resin, such as Amberlyst 15, $P_2O_5$, etc., may be used for dehydration purposes. The temperature and pressure are adjusted to remove water, as by volatilization or absorption. Subatmospheric pressure may be used. Dehydration is followed by hydrogenation with molecular hydrogen under the conditions set forth above for hydrogenolysis. The literature contains many references to these procedures, and to the extent they are compatible with the organic chemicals hereof undergoing hydrogenolysis or dehydration followed by hydrogenation, any of such procedures may be used.

When the aryl addition material is an arylmethyl halide, e.g., p-isopropylbenzyl chloride, the condensation or alkylation product is directly the final product (I) pursuant to the following scheme:

This alkylation reaction may be carried out at relatively moderate temperatures below about 100° C. at ordinary pressures, and is conveniently carried out without application of heat in the presence of a catalytic amount of a copper salt or other metal salt, e.g., CuCl, $Li_2CuCl_4$, etc. Instead of the aldehyde or benzyl halide, we may use those aryl compounds where X in (III) above is replaced with $-OR^3$; $-OCOR^3$; $-NR_3^3$; $-SO_2R^3$; $-OSO_2R^3$; or $-OP(O)(OR^3)_2$ where $R^3$ is lower alkyl, e.g., methyl, ethyl, propyl or butyl. In general, the alkylating agent is used in molar excess over the Grignard exchange product and the extent of such excess is again a matter of convenience bearing in mind recovery of the alkylating agent and the cost of that operation. In general, a molar excess of from 1.1:1 to 2:1 may be used.

It becomes convenient at this point to give illustrative examples of the improved processes of the present invention it being understood that these examples are for illustrative purposes only and are not to be construed as limiting the invention to the scope thereof. Other derivatives or analogues such as described in U.S. Pat. No. 4,002,769 may be made following the same procedures, substituting on an equimolar basis, for example, other p-alkyl substituted benzyl reactants, or other terpenoid hydrocarbon starting materials of a natural or synthetic origin. Such modifications in the light of the following examples will now become evident to those skilled in the art. In these examples all temperatures are in degrees Centigrade. Recovery of the final product is most conveniently by vacuum distillation.

EXAMPLE I

3,7-Dimethyl-7-methoxy-1-octene

A mixture of dihydromyrcene (1123 grams), methanol (290 grams) and Amberlyst A-15 catalyst (36 grams) was stirred at 50°. After 19 hours, another portion of methanol (1160 grams) was added. Reaction continued for four (4) days. Filtration of catalyst and distillation of the liquid gave the methoxy compound (805 grams, 58% yield). The yield was 81% based on unrecovered dihydromyrcene. The catalyst could be reused.

EXAMPLE II

1-(p-Isopropylphenyl)-4,8-dimethyl-8-methoxynonane

To a solution of n-propylmagnesium bromide (0.25 mole) in tetrahydrofuran (200 ml) was added 7- methoxy-3,7-dimethyl-1-octene (42.5 g) and biscyclopentadienyl titanium dichloride (1.25 g). After the vigorous reaction subsided, the mixture was heated in an oil bath (75°) for 19 hours. Aliquot quench at this point indicated ~50% conversion. The Grignard exchange product was transferred to a separatory funnel, and added dropwise to p-isopropylbenzyl chloride (21 g) in THF (300 ml) containing cuprous chloride (2.5 g) cooled at 0° to −10° while stirring. On warming to room temperature overnight, the reaction was then quenched with aqueous ammonium chloride and extracted with pentane. The pentane extracts were distilled to give product (2,6-dimethyl-2-methoxy-9-isopropylphenylnonane) (12.5 g; bp 150°–152° /0.25–0.3 torr) contaminated with some p, p'-diisopropylbibenzyl.

EXAMPLE III 1-(p-Isopropylphenyl)-4,8-dimethyl-8-methoxynonan-1-ol n-Propylmagnesium bromide (0.12 mol) prepared from magnesium (2.9 g) and 1-bromopropane (14.8 g) in ether (100 ml) at room temperature was cooled in an ice bath, while 7-methoxy-3,7-dimethyl-1-octene (7-alkoxy dihydromyrcene) (17 g) and ether (20 ml) were added followed by biscyclopentadienyl titanium dichloride (0.4 g). Vigorous gas evolution ensued. After stirring at room temperature under a nitrogen atmosphere overnight; the Grignard exchange product (~50% conversion as determined by quenching of an aliquot) was treated with p-isopropylbenzaldehyde (14.8 g) in ether (50 ml) and stirring continued for 24 hours. The reaction mixture was quenched with aqueous ammonium chloride and extracted with pentane. The dried pentane solution was evaporated to give an oil (29.4 g) containing 7-methoxy-3,7-dimethyl-1-octene (28.8%) and the desired alcohol product (24.8%) identified by GC-MS as 1-(p-isopropylphenyl)-4,8-dimethyl-8-methoxynonan-1-ol.

EXAMPLE IV 1-(p-Isopropylphenyl)-4,8-dimethyl-8-methoxynonan-1-ol i-Propylmagnesium bromide (0.1 mol) in tetrahydrofuran (50 ml) was treated with 7-methoxy-3,7-dimethyl-1-octene (7-methoxy dihydromyrcene) (8.5 g), and biscyclopentadienyl titanium dichloride (0.3 g). After stirring at room temperature overnight, the resulting Grignard exchange product was reacted with p-isopropylbenzaldehyde (7.5 g). At the end of 4 hours, the reaction mixture was quenched with aqueous ammonium chloride, and then dilute (5%) aqueous hydrochloric acid. Pentane extraction yielded an oil (15.5 g) which contained 26.05% of the desired alcohol product, 1-(p-isopropylphenyl)-4,8-dimethyl-8-methoxynonan-1-ol.

EXAMPLE V 1-(p-Isopropylphenyl)-4,8-dimethyl-8-methoxynonan-1-ol

The procedure of Example IV above is repeated except that 0.1 mole i-propylmagnesium chloride is substituted for the i-propylmagnesium bromide. The same alcohol product is produced and recovered.

EXAMPLE VI 1-(p-Isopropylphenyl)-4,8-dimethyl-7-nonen-1-ol n-Propylmagnesium bromide (0.12 mol) in ether (100 ml) was treated with 3,7-dimethyl-1,6-octadiene (dihydromyrcene) (13.8 g) in ether (20 ml) and biscyclopentadienyl titanium dichloride (0.4 g) under nitrogen without application of heat. After stirring overnight at room temperature, p-isopropylbenzaldehyde (14.8 g) in ether (50 ml) was added. The reaction was allowed to proceed at room temperature for 24 hours, and quenched with aqueous ammonium chloride. Pentane extraction followed by drying and evaporation gave an oil (28 g) which contained 17.5% 3,7-dimethyl-1,6-octadiene and 31.4% of 1-(p-isopropylphenyl)-4,8-dimethyl-7-nonen-1-ol.

EXAMPLE VII 2,6-Dimethyl-9-(p-isopropylphenyl)-2-nonene n-Propylmagnesium bromide (0.12 mol) in ether (50 ml) was treated with 3,7-dimethyl-1,6-octadiene (dihydromyrcene) (13.8 g) and biscyclopentadienyl titanium dichloride ($Cp_2TiCl_2$) (0.5 g) under nitrogen without initial application of heat. After the initial vigorous reaction subsided, the reaction mixture was refluxed for 2 hours, cooled, and transferred to a separatory funnel. The Grignard exchange product was then added slowly to p-isopropylbenzyl chloride (15 g) and cuprous chloride (0.5 g) in tetrahydrofuran (THF) (50 ml) which was cooled in an ice bath. The cooling bath was removed after the addition and stirring was maintained for 14 hours. Addition of water and pentane; draining of the aqueous layer, and subsequent washing of the organic solution with aqueous ammonium hydroxide, water, dil. hydrochloric acid, drying, and evaporation furnished an oil (13.1 g) which contained 30.8% of 2,6-dimethyl-9-(p-isopropylphenyl)-2-nonene according to GC and GC-MS anaylsis.

EXAMPLE VIII 1-(p-Isopropylphenyl)-4,8-dimethyl-8-methoxynonane

The reaction mixture containing 1-(p-isopropylphenyl)-4,8-dimethyl-8-methoxynonan-1-ol as obtained above (Example III) (9.9 g) was submitted to hydrogenolysis by dissolution in an acidic lower alkanol, e.g., methanol (50 ml) and conc. HCl (1 ml) and was then hydrogenated with $H_2$ in the presence of 5% Pd-C (0.4 g). After uptake of hydrogen ceased, the catalyst was removed by filtration with the aid of a filter aid (Celite). The filtrate was washed with aq. $NaHCO_3$, brine and dried over $MgSO_4$. Evaporation of solvent left a yellow oil (8.4 g). Distillation gave the desired product (1-(p-isopropylphenyl)-4,8-dimethyl-8-methoxynonane) (2.8 g, bp. 120°–125°/0.05 torr). The NMR spectrum showed the following signals 1.08 (6H, s), 1.22 (6H, d, J.=6.5 Hz): ($CDCl_3$) 0.88 (3H, d, J=6.5 Hz), 2.60 (2H, t, J=7 Hz), 2.90 (1H, m), 3.14 (3H, s), 7.10 (4H, s).

EXAMPLE IX 1-(p-Isopropylphenyl)-1,8-dimethoxy-4,8-dimethylnonane

Crude 1-(p-isopropylphenyl)-4,8-dimethyl-8-methoxy-1-nonanol (1.1 g) and "Amberlyst A-15" resin (50 mg) in methanol (20 ml), as the acidic lower alkanol, was refluxed for 2 days. GC analysis showed the consumption of the alcohol and appearance of the dimethoxy compound. Material was recovered quantitatively. "Amberlyst A-15" resin used in this methoxylation reaction is a commercially available solid acidic ion exchange resin with pendant sulfonic acid groups.

EXAMPLE X 1-(p-Isopropylphenyl)-4,8-dimethyl-8-methoxynonane

The synthesis of Example II is repeated except for substituting for n-propyl magnesium bromide, 0.25 mole of isopropyl magnesium chloride. The same product is produced and recovered.

EXAMPLE XI 2,6-Dimethyl-2 Methoxy-9-isopropylphenylnonane

This example illustrates post-methoxylation. The crude coupling product (13.0 g) containing 30.8% 2,6-dimethyl-9-(p-isopropylphenyl)-2-nonene was dissolved in an excess of methanol (30 ml) and treated with Amberlyst 15 catalyst (1.0 g). The mixture was stirred and refluxed for 48 h. The catalyst was filtered, and the methanolic solution was evaporated to give an oil (12.4 g) containing 22.7% of the desired product, 2,6-dimethyl-2-methoxy-9-(isopropylphenyl)-nonane.

EXAMPLE XII 2,6-Dimethyl-2-ethoxy-9-(isopropylphenyl)nonane

The procedure of Example X is repeated exactly except for substituting for methanol an equivalent amount of ethanol and the corresponding ethoxy derivative is produced and recovered.

EXAMPLE XIII 2,6-Dimethyl-2-methoxy-9-(isopropylphenyl)-nonane 3,7-Dimethyl-7-methoxyoctylmagnesium bromide (40 mmol) in THF (95 ml) was added during 10 min. to p-isopropylbenzyl mesylate (40 mmol) and cuprous chloride (2 g) in THF (150 ml) while maintaining at −10°. The reaction mixture was allowed to come to room temperature, stirred overnight under a nitrogen blanket, and then quenched with aqueous ammonium chloride. Extraction with pentane gave an oil (14 g) which was distilled at 0.05 torr, bp. 135°–140° to provide the product (2,6-dimethyl-2-methoxy-9-(isopropylphenyl)-nonane) (4.5 g, 38% yield).

EXAMPLE XIV 2,6-Dimethyl-2-methoxy-9-(isopropylphenyl)-nonane 1-(p-Isopropylphenyl)-1,8-dimethoxy-4,8-dimethylnonane (1.1 g) and 5% Pd-on-carbon catalyst (20 mg), conc. HCl (0.5 ml) in methanol (20 ml) were hydrogenated in a Parr shaker overnight. Filtration of the catalyst, evaporation of solvent, neutralization of the acid then provide the methoxy depleted monomethoxy product, 2,6-dimethyl-2-methoxy-9-(isopropylphenyl)-nonane.

EXAMPLE XV 3,7-Dimethyl-7-thiomethoxy-1-octene

The procedure of example I is repeated using an equivalent amount methylmercaptan in place of methanol. The thio-derivative is recovered.

EXAMPLE XVI

7-Methoxy-3,7-dimethyl-octylmagnesium Chloride i-Propylmagnesium chloride (0.5 mol) in tetrahydrofuran (200 ml) was treated with 7-methoxy-3,7-dimethyl-1-octene (85 g), followed by dropwise addition of a tri-isobutyl vanadate (7.0 g) in tetrahydrofuran (40 ml) at room temperature. The reaction mixture was then refluxed under nitrogen for 5 h when an aliquot showed a 72% conversion and 87% theoretical yield of the Grignard reagent.

EXAMPLE XVII 1-(p-Isopropylphenyl)-4,8-dimethyl-8-methoxynonane

A solution of 7-methoxy-3,7-dimethyloctylmagnesium chloride (0.155 mol) in tetrahydrofuran (200 ml) was added dropwise to a rapidly stirred mixture of p-isopropylbenzyl chloride (26 g) and cuprous chloride (10 g) in tetrahydrofuran (100 ml) under nitrogen and cooled at −15°-−20°, over 40 min. After gradual warming to room temperature and keeping for 22 h, the reaction mixture was poured into saturated ammonium chloride solution, and extracted with pentane. The extracts were washed with dilute ammonium hydroxide, dried, concentrated to give 55 g crude product containing 1-(p-isopropyl-phenyl)-4,8-dimethyl-8-methoxynonane as the major component.

EXAMPLE XVIII 1-(p-Isopropylphenyl)-4,8-dimethyl-8-methoxynonan-1-ol

To the 7-methoxy-3,7-dimethyloctylmagnesium chloride (0.155 mol) in tetrahydrofuran (200 ml) under nitrogen was added p-isopropylbenzaldehyde (37 g, 86.94% pure) in tetrahydrofuran (50 ml) over 20 min. The reaction was exothermic, causing solvent to boil during the course of addition. After stirring at room temperature continued thereafter for a total of 23 h, the reaction mixture was poured into dilute hydrochloric acid, and extracted with pentane. The extracts were washed with bicarbonate, brine, and dried. Upon solvent evaporation, an oil weighing 65.1 g was obtained which was shown to contain 18.31% of the alcohol product.

The Grignard exchange reaction with 1 equivalent of propylmagnesium bromide yields about 50% conversion. Experience has shown that using 2 equivalents of propylmagnesium bromide, a 92% conversion is attained in tetrahydrofuran solvent.

From the foregoing examples, those skilled in the art have been taught how to make certain arylterpenoid compounds from an inexpensive source material, namely pinene, and further by employing a little known Grignard exchange reaction, to eliminate a substantial number of steps in the production of such arylterpenoid compounds identified, produced and used as described in the aforesaid U.S. Pat. No. 4,002,769. With the procedures fully described as above, those skilled in the art will now be able to synthesize analogous compounds, e.g., those having other alkyl/aryl or alkoxy substituents and to utilize equivalent Grignard reagents, e.g., chlorides in lieu of bromides, or equivalent Grignard exchange catalysts, e.g., TiCl$_4$ or vanadium tetrachloride or biscyclopentadienyl titanium dichloride or NiCl$_2$, etc.

The best mode of carrying out our process known to us at this time is from pinane by pressure hydrogenating (50–80 psig.) alpha- or beta pinene, or a mixture thereof, with hydrogen until 1 mole H$_2$/mole pinene is absorbed using a solid contact catalyst such as Raney nickel catalyst, to form pinane. Pinane is recovered by distillation. Pinane results from hydrogenation of either alpha- or beta-pinene or a mixture thereof. The pinane is then pyrolyzed at a temperature above 200° C., for example, 600°–620° C. by vaporizing the pinane and passing it through a 0.5 inch metal tube at the rate of 0.25 gram/minute of liquid condensate. (See U.S. Pat. No. 2,902,495, Examples I and II.). This results in dihydromyrcene, or 3,7-dimethyl-1,6-octadiene, or citronellene (CA Reg. No. 2436-90-0) which can be recovered by distillation.

Other more costly methods of making dihydromyrcene are known.

The dihydromyrcene is then methoxylated as described in Example I to form 7-methoxy-3,7-dimethyl-1-octene. Then according to Example II, the Grignard exchange product is formed and alkylated with p-isopropylbenzyl chloride to form the final product, 2,6-dimethyl-2-methoxy-9-isopropylphenyl nonane. The final product is recovered by vacuum distillation. To reduce expenses, the isopropyl magnesium chloride Grignard may advantageously be substituted for the n-propyl magnesium bromide.

What is claimed is:

1. A process for making a biologically active 2,6-dimethyl-2-alkoxy-9-aryl nonane which comprises the steps of:
   (a) reacting at a temperature below about 50° C. a 3,7-dimethyl-7-alkoxy-1-octene with a lower alkyl Grignard in the presence of a Grignard exchange catalyst for a period of time sufficient to evolve substantially 1 mole of alkene per mole of 3,7-dimethyl-7-alkoxy-1-octene and form a Grignard exchange product and release a lower alkylene hydrocarbon;
   (b) benzylating at a temperature of from −10° C. to 30° C. the resulting Grignard exchange product to form a 2,6-dimethyl-2-alkoxy-9-aryl nonane; and
   (c) recovering from the previous step a 2,6-dimethyl-2-alkoxy-9-aryl nonane material;
in which material the aryl group contains at least one substituent attached to a ring carbon atom and is selected from lower alkyl, lower alkoxy, and lower thioalkoxy.

2. A process as defined in claim 1 wherein the benzylating step is carried out using a benzyl halide.

3. A process as defined in claim 1 wherein the benzylating step is carried out using a substituted benzyl chloride.

4. A process as defined in claim 3 wherein the substituted benzyl chloride is p-isopropyl benzyl chloride.

5. A process as defined in claim 1 wherein the lower alkyl Grignard is an n-propyl magnesium halide.

6. A process as defined in claim 5 wherein the n-propyl magnesium halide is n-propyl magnesium bromide.

7. A process as defined in claim 5 wherein the n-propyl magnesium halide is n-propyl magnesium chloride.

8. A process as defined in claim 1 wherein the lower alkyl Grignard is isopropyl magnesium bromide.

9. A process as defined in claim 1 wherein the lower alkyl Grignard is isopropyl magnesium chloride.

10. A process as defined in claim 1 wherein the lower alkyl Grignard is ethyl magnesium bromide.

11. A process as defined in claim 1 wherein the Grignard exchange catalyst is TiCl$_4$.

12. A process as defined in claim 1 wherein the Grignard exchange catalyst is biscyclopentadiene titanium dichloride.

13. A process as defined in claim 1 wherein the Grignard exchange catalyst is tri-isobutyl vanadate.

14. A process as defined in claim 1 wherein the Grignard exchange catalyst is nickel chloride.

15. A process as defined in claim 1 wherein the benzylating step is carried out using a benzaldehyde.

16. A process as defined in claim 15 which is further characterized by steps of (d) dehydrating the benzylated product and (e) hydrogenating the product of step (d) to form the 2,6-dimethyl-2-alkoxy-9-aryl nonane as defined in step (c).

17. A process as defined in claim 15 which is further characterized by the step of (d) hydrogenolysis to form the 2,6-dimethyl-2-alkoxy-9-aryl nonane.

18. A process as defined in claim 16 wherein the benzaldehyde is p-isopropylbenzaldehyde.

19. A process for making a biologically active 2,6-dimethyl-2-alkoxy-9-aryl nonane which comprises the steps of:
   (a) reacting at a temperature below about 50° C. 3,7-dimethyl-1,6-octadiene with a lower alkyl Grignard reagent in the presence of a Grignard exchange catalyst to form a Grignard exchange product and release lower alkylene hydrocarbon for a period of time sufficient to evolve substantially one mole of alkene per mole of 3,7-dimethyl-1,6-octadiene;
   (b) benzylating at a temperature of from about −10° C. to about 30° C. the resulting Grignard exchange product to form a 2,6-dimethyl-9-aryl-2-nonene;
   (c) alkoxylating the olefinic bond of the product of step (b) with a molar excess of an acidic lower alkanol containing from 1 to 4 carbons to form a 2,6-dimethyl-2-alkoxy-9-aryl nonane; and
   (d) recovering said 2,6-dimethyl-2-alkoxy-9-aryl nonane material in which material the alkoxy group is a lower alkoxy group, and the aryl group contains at least one substituent attached to a ring carbon atom and is selected from lower alkyl, lower alkoxy and lower thioalkoxy.

20. A process as defined in claim 19 wherein the benzylating step is carried out using a benzyl halide.

21. A process as defined in claim 19 wherein the benzylating step is carried out using a substituted benzyl chloride.

22. A process as defined in claim 21 wherein the substituted benzyl chloride is p-isopropyl benzyl chloride.

23. A process as defined in claim 19 wherein the lower alkyl Grignard is an n-propyl magnesium halide.

24. A process as defined in claim 19 wherein the lower alkyl Grignard is isopropyl magnesium bromide.

25. A process as defined in claim 19 wherein the lower alkyl Grignard is isopropyl magnesium chloride.

26. A process as defined in claim 19 wherein the lower alkyl Grignard is ethyl magnesium bromide.

27. A process as defined in claim 23 wherein the n-propyl magnesium halide is n-propyl magnesium chloride.

28. A process as defined in claim 19 wherein the Grignard exchange catalyst is TiCl$_4$.

29. A process as defined in claim 19 wherein the Grignard exchange catalyst is tri-isobutyl vanadate.

30. A process as defined in claim 19 wherein the Grignard exchange catalyst is biscyclopentadiene titanium dichloride.

31. A process as defined in claim 19 wherein the Grignard exchange catalyst is zirconium tetrachloride.

32. A process as defined in claim 19 wherein the Grignard exchange catalyst is nickel chloride.

33. A process as defined in claim 19 wherein the benzylating step is carried out using a benzaldehyde.

34. A process as defined in claim 33 which is further characterized by the steps of (e) dehydrating the benzylated product and (f) hydrogenating the product of step (e) to form the 2,6-dimethyl-2-alkoxy-9-aryl nonane material as defined in step (d).

35. A process as defined in claim 33 which is further characterized by the step of (e) hydrogenolysis to form the 2,6-dimethyl-2-alkoxy-9-aryl nonane.

36. A process for making a biologically active 2,6-dimethyl-2-lower alkoxy-9-(p-lower alkyl phenyl)-nonane comprising the steps of:
 (a) hydrogenating with molecular hydrogen in the presence of a solid hydrogenation catalyst, alpha- or beta-pinene or a mixture thereof to obtain pinane;
 (b) pyrolyzing said pinane in the vapor phase at a temperature above 200° C. to form 3,7-dimethyl-1,6-octadiene;
 (c) reacting said 3,7-dimethyl-1,6-octadiene with a molar excess of an acidic lower alkanol under reflux conditions to form 3,7-dimethyl-7-alkoxy-octene-1;
 (d) reacting at a temperature below about 50° C. said 3,7-dimethyl-7-alkoxy-octene-1 with RMgX where R is n-propyl or isopropyl and X is halogen, in the presence of a Grignard exchange catalyst to exchange the R group with the terminal carbon atom of said octene-1 compound for a period of time sufficient to evolve substantially 1 mole of alkene per mole of 3,7-dimethyl-7-alkoxy-1-octene to form 3,7-dimethyl-7-alkoxy-octyl magnesium halide;
 (e) benzylating at a temperature of from −10° C. to 30° C. said 3,7-dimethyl-7-alkoxy-octyl magnesium halide with p-lower alkyl benzyl halide or p-lower alkyl benzaldehyde to form a 2,6-dimethyl-1-alkoxy-9-aryl nonane or a 2,6-dimethyl-1-alkoxy-9-aryl nonane-1-ol; and
 (f) recovering 2,6-dimethyl-2-lower alkoxy-9-(p-lower alkyl phenyl)-nonane from the reaction mass.

37. A process for making a biologically active 2,6-dimethyl-2-lower alkoxy-9-(p-lower alkyl phenyl)-nonane comprising the steps of:
 (a) hydrogenating with molecular hydrogen alpha- or beta-pinene, or a mixture thereof, in the presence of a solid hydrogenation catalyst to obtain pinane;
 (b) pyrolyzing said pinane in the vapor phase at a temperature above 200° C. to form 3,7-dimethyl-1,6-octadiene;
 (c) reacting at a temperature below about 50° C. said 3,7-dimethyl-1,6-octadiene with $R^4$MgX wherein $R^4$ is n-propyl or isopropyl or ethyl and X is halogen, in the presence of a vanadium, zirconium, titanium, nickel, iron, or cobalt Grignard exchange catalyst to exchange the $R^4$ group with the terminal olefinic linkage of the diene to form 3,7-dimethyl-6-octenyl magnesium halide for a period of time sufficient to evolve substantially one mole of alkene per mole of 3,7-dimethyl-1,6-octadiene;
 (d) reacting at a temperature of −10° C. to about 30° C. said 3,7-dimethyl-6-octenyl magnesium halide with p-lower alkyl benzyl chloride; to form 2,6-dimethyl-9-(p-lower alkyl phenyl)-2-nonene;
 (e) alkoxylating said 2,6-dimethyl-9-(p-lower alkyl phenyl)-2-nonene by reaction with a molar excess of acidic lower alkanol containing from 1 to 4 carbons and at a temperature below about 110° C. to form a 2,6-dimethyl-2-alkoxy-9-(p-lower alkyl phenyl)nonane; and
 (f) recovering said 2,6-dimethyl-2-alkoxy-9-(p-lower alkyl phenyl)-nonane from the reaction mass.

38. A process as defined in claim 36 in which the lower alkanol is a $C_1$–$C_4$ alcohol.

39. A process as defined in claim 37 in which the lower alkanol is a $C_1$–$C_4$ alcohol.

40. A process as defined in claim 36 in which the lower alkanol is methanol.

41. A process as defined in claim 37 in which the lower alkanol is methanol.

42. A process as defined in claim 36 in which the lower alkyl substituted phenyl group is a $C_1$–$C_4$ alkyl phenyl group.

43. A process as defined in claim 37 in which the lower alkyl substituted phenyl group is a $C_1$–$C_4$ alkyl phenyl group.

44. A process as defined in claim 42 in which the $C_1$–$C_4$ alkyl group is isopropyl.

45. A process as defined in claim 37 in which the $C_1$–$C_4$ alkyl group is isopropyl.

46. A process as defined in claim 36 wherein the Grignard exchange catalyst is $TiCl_4$.

47. A process as defined in claim 36 wherein the Grignard exchange catalyst is biscyclopentadiene titanium dichloride.

48. A process as defined in claim 36 wherein the Grignard exchange catalyst is $NiCl_2$.

49. A process for making a biologically active 2,6-dimethyl-2-lower alkoxy-9-(p-lower alkyl phenyl)-nonane comprising the steps of:
 (a) hydrogenating with molecular hydrogen alpha- or beta-pinene, or a mixture thereof, in the presence of a solid hydrogenation catalyst to obtain pinane;
 (b) pyrolyzing said pinane in the vapor phase at a temperature above 200° C. to form 3,7-dimethyl-1,6-octadiene;
 (c) reacting at a temperature below about 50° C. said 3,7-dimethyl-1,6-octadiene with $R^4$MgX wherein $R^4$ is n-propyl or isopropyl or ethyl and X is halogen, in the presence of a vanadium, zirconium, titanium, nickel, iron, or cobalt catalyst to exchange the $R^4$ group with the terminal olefinic linkage of the diene to form 3,7-dimethyl-6-octenyl magnesium halide for a period of time sufficient to evolve substantially one mole of alkene per mole of 3,7-dimethyl-1,6-octadiene;
 (d) reacting said 3,7-dimethyl-6-octenyl magnesium halide with a p-lower alkyl benzaldehyde to form a 2,6-dimethyl-2-alkoxy-9-(p-lower alkylphenyl)nonane-1-ol;
 (e) dehydrating and hydrogenating the product of step (d) above;
 (f) benzylating at a temperature of from −10° C. to 30° C. said 3,7-dimethyl-7-alkoxy-octyl magnesium halide with p-lower alkyl benzyl halide or p-lower alkyl benzaldehyde to form a 2,6-dimethyl-2-alkoxy-9-aryl nonane or a 2,6-dimethyl-1-alkoxy-9-aryl nonane-1-ol; and
 (g) recovering said 2,6-dimethyl-2-alkoxy-9-(p-lower alkyl phenyl)-nonane from the reaction mass.

* * * * *